US012262964B2

(12) United States Patent
Rosenberg et al.

(10) Patent No.: US 12,262,964 B2
(45) Date of Patent: Apr. 1, 2025

(54) ROBOTIC SURGICAL INSTRUMENT INCLUDING LINEAR ENCODERS FOR MEASURING CABLE DISPLACEMENT

(71) Applicant: Covidien LP, Mansfield, MA (US)

(72) Inventors: Meir Rosenberg, Newton, MA (US); William J. Peine, Ashland, MA (US)

(73) Assignee: Covidien LP, Mansfield, MA (US)

( * ) Notice: Subject to any disclaimer, the term of this patent is extended or adjusted under 35 U.S.C. 154(b) by 293 days.

(21) Appl. No.: 17/794,302

(22) PCT Filed: Feb. 4, 2021

(86) PCT No.: PCT/US2021/016497
§ 371 (c)(1),
(2) Date: Jul. 21, 2022

(87) PCT Pub. No.: WO2021/173315
PCT Pub. Date: Sep. 2, 2021

(65) Prior Publication Data
US 2023/0084237 A1   Mar. 16, 2023

Related U.S. Application Data

(60) Provisional application No. 62/981,735, filed on Feb. 26, 2020.

(51) Int. Cl.
*A61B 34/30* (2016.01)
*A61B 17/29* (2006.01)
(Continued)

(52) U.S. Cl.
CPC .............. *A61B 34/30* (2016.02); *A61B 17/29* (2013.01); *A61B 34/71* (2016.02);
(Continued)

(58) Field of Classification Search
CPC ......... A61B 34/30; A61B 34/71; A61B 17/29; A61B 2034/2059; A61B 2034/305; A61B 2090/061; G05B 2219/37154
See application file for complete search history.

(56) References Cited

U.S. PATENT DOCUMENTS 6,132,368 A   10/2000 Cooper
6,206,903 B1   3/2001 Ramans
(Continued)

FOREIGN PATENT DOCUMENTS

WO   2013002414 A1   1/2013
WO   2017053358 A1   3/2017

OTHER PUBLICATIONS

International Search Report mailed May 25, 2021 and Written Opinion completed May 10, 2021 corresponding to counterpart Int'l Patent Application PCT/US2021/016497.

*Primary Examiner* — Thomas E Worden
*Assistant Examiner* — Benjamin J Brosh
(74) *Attorney, Agent, or Firm* — Carter, DeLuca & Farrell LLP (57) ABSTRACT

An electromechanical robotic surgical instrument is provided and includes a flexible shaft defining a lumen therethrough; an end effector pivotally supported by the flexible shaft; at least one cable translatably disposed within the lumen of the flexible shaft, wherein a distal end of each cable is operatively connected to the end effector to affect a movement of the end effector in response to translation of the at least one cable, wherein the at least one cable includes metrical markings along an outer surface thereof, which metrical markings are located adjacent to the end effector; and at least one linear encoder supported by the flexible shaft and being in operative registration with the metrical markings of a respective one of the at least one cable, wherein the
(Continued)

at least one linear encoder is configured to measure changes in the metrical markings.

13 Claims, 7 Drawing Sheets (51) Int. Cl.
*A61B 34/00* (2016.01)
*A61B 34/20* (2016.01)
*A61B 90/00* (2016.01)

(52) U.S. Cl.
CPC . *A61B 2034/2059* (2016.02); *A61B 2034/305* (2016.02); *A61B 2090/061* (2016.02)

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 * | 4/2010 | Whitman ......... A61B 17/07207 606/142 |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |

(56) References Cited

U.S. PATENT DOCUMENTS

| | | | |
|---|---|---|---|
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,666,544 | B2 | 3/2014 | Moll et al. |
| 8,668,638 | B2 | 3/2014 | Donhowe et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,808,164 | B2 | 8/2014 | Hoffman et al. |
| 8,816,628 | B2 | 8/2014 | Nowlin et al. |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,852,174 | B2 | 10/2014 | Burbank |
| 8,858,547 | B2 | 10/2014 | Brogna |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,903,546 | B2 | 12/2014 | Diolaiti et al. |
| 8,903,549 | B2 | 12/2014 | Itkowitz et al. |
| 8,911,428 | B2 | 12/2014 | Cooper et al. |
| 8,912,746 | B2 | 12/2014 | Reid et al. |
| 8,944,070 | B2 | 2/2015 | Guthart |
| 8,989,903 | B2 | 3/2015 | Weir et al. |
| 9,002,518 | B2 | 4/2015 | Manzo |
| 9,014,856 | B2 | 4/2015 | Manzo et al. |
| 9,016,540 | B2 | 4/2015 | Whitman et al. |
| 9,019,345 | B2 | 4/2015 | O'Grady et al. |
| 9,043,027 | B2 | 5/2015 | Durant et al. |
| 9,050,120 | B2 | 6/2015 | Swarup et al. |
| 9,055,961 | B2 | 6/2015 | Manzo et al. |
| 9,068,628 | B2 | 6/2015 | Solomon et al. |
| 9,078,684 | B2 | 7/2015 | Williams |
| 9,084,623 | B2 | 7/2015 | Gomez et al. |
| 9,095,362 | B2 | 8/2015 | Dachs et al. |
| 9,096,033 | B2 | 8/2015 | Holop et al. |
| 9,101,381 | B2 | 8/2015 | Burbank et al. |
| 9,113,877 | B1 | 8/2015 | Whitman et al. |
| 9,138,284 | B2 | 9/2015 | Krom et al. |
| 9,144,456 | B2 | 9/2015 | Rosa et al. |
| 9,198,730 | B2 | 12/2015 | Prisco et al. |
| 9,204,923 | B2 | 12/2015 | Manzo et al. |
| 9,226,648 | B2 | 1/2016 | Saadat et al. |
| 9,226,750 | B2 | 1/2016 | Weir et al. |
| 9,226,761 | B2 | 1/2016 | Burbank |
| 9,232,984 | B2 | 1/2016 | Guthart et al. |
| 9,241,766 | B2 | 1/2016 | Duque et al. |
| 9,241,767 | B2 | 1/2016 | Prisco et al. |
| 9,241,769 | B2 | 1/2016 | Larkin et al. |
| 9,259,275 | B2 | 2/2016 | Burbank |
| 9,259,277 | B2 | 2/2016 | Rogers et al. |
| 9,259,281 | B2 | 2/2016 | Griffiths et al. |
| 9,259,282 | B2 | 2/2016 | Azizian et al. |
| 9,261,172 | B2 | 2/2016 | Solomon et al. |
| 9,265,567 | B2 | 2/2016 | Orban, III et al. |
| 9,265,584 | B2 | 2/2016 | Itkowitz et al. |
| 9,283,049 | B2 | 3/2016 | Diolaiti et al. |
| 9,301,811 | B2 | 4/2016 | Goldberg et al. |
| 9,314,307 | B2 | 4/2016 | Richmond et al. |
| 9,317,651 | B2 | 4/2016 | Nixon |
| 9,345,546 | B2 | 5/2016 | Toth et al. |
| 9,393,017 | B2 | 7/2016 | Flanagan et al. |
| 9,402,689 | B2 | 8/2016 | Prisco et al. |
| 9,417,621 | B2 | 8/2016 | Diolaiti |
| 9,424,303 | B2 | 8/2016 | Hoffman et al. |
| 9,433,418 | B2 | 9/2016 | Whitman et al. |
| 9,446,517 | B2 | 9/2016 | Burns et al. |
| 9,452,020 | B2 | 9/2016 | Griffiths et al. |
| 9,474,569 | B2 | 10/2016 | Manzo et al. |
| 9,480,533 | B2 | 11/2016 | Devengenzo et al. |
| 9,503,713 | B2 | 11/2016 | Zhao et al. |
| 9,550,300 | B2 * | 1/2017 | Danitz ............... A61B 1/0053 |
| 9,554,859 | B2 | 1/2017 | Nowlin et al. |
| 9,566,124 | B2 | 2/2017 | Prisco et al. |
| 9,579,164 | B2 | 2/2017 | Itkowitz et al. |
| 9,585,641 | B2 | 3/2017 | Cooper et al. |
| 9,615,883 | B2 | 4/2017 | Schena et al. |
| 9,623,563 | B2 | 4/2017 | Nixon |
| 9,623,902 | B2 | 4/2017 | Griffiths et al. |
| 9,629,520 | B2 | 4/2017 | Diolaiti |
| 9,662,177 | B2 | 5/2017 | Weir et al. |
| 9,664,262 | B2 | 5/2017 | Donlon et al. |
| 9,675,354 | B2 | 6/2017 | Weir et al. |
| 9,687,312 | B2 | 6/2017 | Dachs, II et al. |
| 9,700,334 | B2 | 7/2017 | Hinman et al. |
| 9,718,190 | B2 | 8/2017 | Larkin et al. |
| 9,730,719 | B2 | 8/2017 | Brisson et al. |
| 9,737,199 | B2 | 8/2017 | Pistor et al. |
| 9,795,446 | B2 | 10/2017 | DiMaio et al. |
| 9,797,484 | B2 | 10/2017 | Solomon et al. |
| 9,801,690 | B2 | 10/2017 | Larkin et al. |
| 9,814,530 | B2 | 11/2017 | Weir et al. |
| 9,814,536 | B2 | 11/2017 | Goldberg et al. |
| 9,814,537 | B2 | 11/2017 | Itkowitz et al. |
| 9,820,823 | B2 | 11/2017 | Richmond et al. |
| 9,827,059 | B2 | 11/2017 | Robinson et al. |
| 9,830,371 | B2 | 11/2017 | Hoffman et al. |
| 9,839,481 | B2 | 12/2017 | Blumenkranz et al. |
| 9,839,487 | B2 | 12/2017 | Dachs, II |
| 9,850,994 | B2 | 12/2017 | Schena |
| 9,855,102 | B2 | 1/2018 | Blumenkranz |
| 9,855,107 | B2 | 1/2018 | Labonville et al. |
| 9,872,737 | B2 | 1/2018 | Nixon |
| 9,877,718 | B2 | 1/2018 | Weir et al. |
| 9,883,920 | B2 | 2/2018 | Blumenkranz |
| 9,888,974 | B2 | 2/2018 | Niemeyer |
| 9,895,813 | B2 | 2/2018 | Blumenkranz et al. |
| 9,901,408 | B2 | 2/2018 | Larkin |
| 9,918,800 | B2 | 3/2018 | Itkowitz et al. |
| 9,943,375 | B2 | 4/2018 | Blumenkranz et al. |
| 9,948,852 | B2 | 4/2018 | Lilagan et al. |
| 9,949,798 | B2 | 4/2018 | Weir |
| 9,949,802 | B2 | 4/2018 | Cooper |
| 9,952,107 | B2 | 4/2018 | Blumenkranz et al. |
| 9,956,044 | B2 | 5/2018 | Gomez et al. |
| 9,980,778 | B2 | 5/2018 | Ohline et al. |
| 10,008,017 | B2 | 6/2018 | Itkowitz et al. |
| 10,028,793 | B2 | 7/2018 | Griffiths et al. |
| 10,033,308 | B2 | 7/2018 | Chaghajerdi et al. |
| 10,034,719 | B2 | 7/2018 | Richmond et al. |
| 10,052,167 | B2 | 8/2018 | Au et al. |
| 10,085,811 | B2 | 10/2018 | Weir et al. |
| 10,092,344 | B2 | 10/2018 | Mohr et al. |
| 10,123,844 | B2 | 11/2018 | Nowlin |
| 10,188,471 | B2 | 1/2019 | Brisson |
| 10,201,390 | B2 | 2/2019 | Swarup et al. |
| 10,213,202 | B2 | 2/2019 | Flanagan et al. |
| 10,258,359 | B2 | 4/2019 | Kapadia |
| 10,258,416 | B2 | 4/2019 | Mintz et al. |
| 10,278,782 | B2 | 5/2019 | Jarc et al. |
| 10,278,783 | B2 | 5/2019 | Itkowitz et al. |
| 10,282,881 | B2 | 5/2019 | Itkowitz et al. |
| 10,335,242 | B2 | 7/2019 | Devengenzo et al. |
| 10,390,853 | B2 | 8/2019 | Kapadia |
| 10,405,934 | B2 | 9/2019 | Prisco et al. |
| 10,433,922 | B2 | 10/2019 | Itkowitz et al. |
| 10,464,219 | B2 | 11/2019 | Robinson et al. |
| 10,485,621 | B2 | 11/2019 | Morrissette et al. |
| 10,500,004 | B2 | 12/2019 | Hanuschik et al. |
| 10,500,005 | B2 | 12/2019 | Weir et al. |
| 10,500,007 | B2 | 12/2019 | Richmond et al. |
| 10,507,066 | B2 | 12/2019 | DiMaio et al. |
| 10,510,267 | B2 | 12/2019 | Jarc et al. |
| 10,524,871 | B2 | 1/2020 | Liao |
| 10,548,459 | B2 | 2/2020 | Itkowitz et al. |
| 10,575,909 | B2 | 3/2020 | Robinson et al. |
| 10,592,529 | B2 | 3/2020 | Hoffman et al. |

(56) References Cited

U.S. PATENT DOCUMENTS

| | | |
|---|---|---|
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | Mcdonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Piolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2010/0211003 A1* | 8/2010 | Sundar .................. A61M 5/172 604/67 |
| 2013/0137963 A1* | 5/2013 | Olson .................... G16H 20/40 600/534 |
| 2014/0039519 A1* | 2/2014 | Inoue .................... A61B 34/37 901/8 |
| 2015/0297199 A1 | 10/2015 | Nicholas et al. |
| 2016/0074120 A1* | 3/2016 | Farritor ............. A61B 17/2909 606/205 |
| 2016/0242779 A1 | 8/2016 | Aranyi et al. |
| 2018/0193100 A1* | 7/2018 | Larkin .................. A61B 34/30 |
| 2018/0193103 A1* | 7/2018 | Haraguchi ......... A61B 1/00193 |
| 2019/0021756 A1* | 1/2019 | Boudreaux ...... A61B 17/00234 |
| 2019/0142531 A1* | 5/2019 | Wentworth ............ A61B 34/30 606/130 |

* cited by examiner

ROBOTIC SURGICAL INSTRUMENT INCLUDING LINEAR ENCODERS FOR MEASURING CABLE DISPLACEMENT

CROSS-REFERENCE TO RELATED APPLICATIONS

The present application is a U.S. National Stage Application filed under 35 U.S.C. § 371(a) claiming the benefit of and priority to International Patent Application No. PCT/US2021/016497, filed Feb. 4, 2021, which claims the benefit of and priority to U.S. Provisional Patent Application Ser. No. 62/981,735, filed Feb. 26, 2020, the entire disclosures of each of which being incorporated by reference herein.

BACKGROUND

Robotic surgical systems have been used in minimally invasive medical procedures. Some robotic surgical systems include a console supporting a surgical robotic arm and a surgical instrument having at least one end effector (e.g., a forceps or a stapling device) mounted to the robotic arm. The robotic arm provides mechanical power to the surgical instrument for its operation and movement. Each robotic arm may include an instrument drive unit that is operatively connected to the surgical instrument. The surgical instruments may include cables that are motor driven to operate flexible or articulatable end effectors of the surgical instruments.

One of the difficulties in controlling flexible surgical instruments stems from the fact that there is no 1:1 translation of controller commands to the effected movement at or near an actuator end of the surgical instrument. This effect is also present in straight/rigid instruments and stems primarily from cable tension elongating the cable and, in turn, reducing the desired movement at the actuator end (e.g., end effector). This effect is further amplified in tool control for flexible surgical instruments where changes to the tool position and shape of the flexible neck translate to cable tension changes which amplify a capstan effect friction, and which also increases as the flexible surgical instrument bends. The real nonlinear behavior is caused by the combination of the friction and the cable stretching, which leads to partial motion of the cable along the length of the surgical instrument shaft and/or flexible neck thereof. This effect is compensated for by measuring the cable tension and using heuristics for the required compensation based on the applied tension to the cable(s).

Accordingly, a need exists for a system which reduces the incidences and effects of tension acting on the cables of robotic surgical instruments and the like.

SUMMARY

The present disclosure relates to robotic surgical systems and/or instruments, and methods for operating the same. According to an aspect of the present disclosure, an electromechanical robotic surgical instrument is provided and includes a flexible shaft defining a lumen therethrough; an end effector pivotally supported by the flexible shaft; at least one cable translatably disposed within the lumen of the flexible shaft, wherein a distal end of each cable is operatively connected to the end effector to affect a movement of the end effector in response to translation of the at least one cable, wherein the at least one cable includes metrical markings along an outer surface thereof, which metrical markings are located adjacent to the end effector; and at least one linear encoder supported by the flexible shaft and being in operative registration with the metrical markings of a respective one of the at least one cable, wherein the at least one linear encoder is configured to measure changes in the metrical markings.

The electromechanical robotic surgical instrument may further include a capsule interconnecting the end effector and a distal end of the flexible shaft, wherein the metrical markings of the at least one cable are disposed within the capsule.

The at least one linear encoder may be disposed within the capsule.

The end effector may be in sealed engagement with the capsule.

The distal end of the flexible shaft may be in sealed engagement with the capsule.

The at least one linear encoder may be configured to command a change in a translation of the at least one cable based on changes exhibited by the metrical markings.

According to another aspect of the present disclosure, a nonlinear control and sensing scheme for an electromechanical robotic surgical instrument is provided. The electromechanical robotic surgical instrument may be the electromechanical robotic surgical instrument described above. The nonlinear control and sensing scheme for the electromechanical robotic surgical instrument includes generating, by a motion controller of a robotic surgical system, a desired position of the end effector; sending a signal, containing the desired position of the end effector, to an end effector position controller; comparing the desired position of the end effector to an actual position of the end effector as measured by a displacement sensor; computing a position error between the desired position and the actual position of the end effector; combining the position error with additional control signals inputs for a nonlinear model for the at least one cable, wherein the nonlinear model determines a desired displacement of a proximal end of the at least one cable to overcome at least one of nonlinearities or changes in a length of the at least one cable; and inputting the desired displacement of the proximal end of the at least one cable to an actuator for translating the at least one cable.

BRIEF DESCRIPTION OF THE DRAWINGS

The accompanying drawings, which are incorporated in and constitute a part of this specification, illustrate embodiments of the present surgical instruments for robotic surgical systems and, together with a general description of the disclosure given above, and the detailed description of the embodiment(s) given below, serve to explain the principles of the disclosure, wherein.

DETAILED DESCRIPTION

Embodiments of the present surgical instruments for robotic surgical systems are described in detail with reference to the drawings, in which like reference numerals designate identical or corresponding elements in each of the several views. As used herein, the term "distal" refers to structure that is closer to a patient, while the term "proximal" refers to structure farther from the patient.

As used herein, the term "clinician" refers to a doctor, nurse, or other care provider and may include support personnel. In the following description, well-known functions or constructions are not described in detail to avoid obscuring the present disclosure in unnecessary detail.

Figure 1:
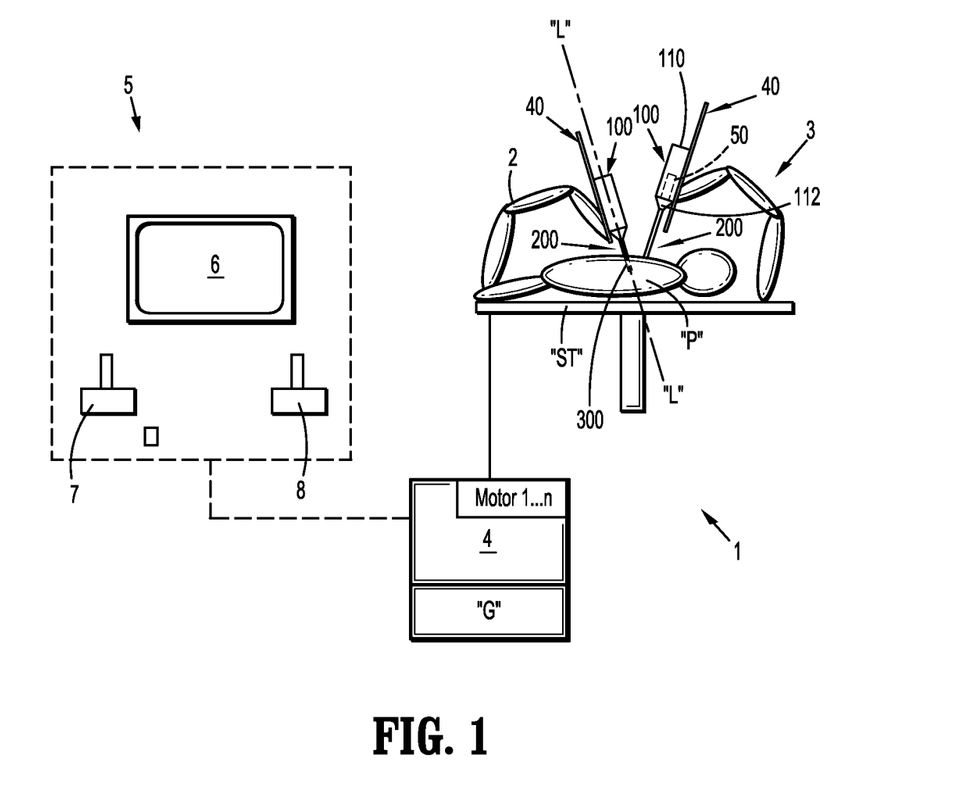
FIG. 1 is a schematic illustration of a robotic surgical system in accordance with the present disclosure.

Referring initially to FIG. 1, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 100 and an electromechanical surgical instrument 200 coupled thereto. Electromechanical surgical instrument 200 includes an end effector 300, in the form of a surgical stapler, disposed at a distal portion thereof. In some embodiments, robotic surgical assembly 100 may be removably attached to a slide rail 40 of one or more of surgical robotic arms 2, 3. In certain embodiments, robotic surgical assembly 100 may be fixedly attached to slide rail 40 of one or more of surgical robotic arms 2, 3.

Operating console 5 of robotic surgical system 1 includes a display device 6, which is set up to display three-dimensional images; and manual input devices 7, 8, by means of which a clinician (not shown), is able to telemanipulate the robotic arms 2, 3 of robotic surgical system 1 in a first operating mode, as known in principle to a person skilled in the art. Each robotic arm of robotic arms 2, 3 may be composed of any number of members, which may be connected through any number of joints. Robotic arms 2, 3 may be driven by electric drives (not shown) that are connected to control device 4. Control device 4 (e.g., a computer) of robotic surgical system 1 is set up to activate the drives, for example, by means of a computer program, in such a way that robotic arms 2, 3, the attached robotic surgical assembly 100, and thus electromechanical surgical instrument 200 (including end effector 300) of robotic surgical system 1 execute a desired movement according to a movement defined by means of manual input devices 7, 8. Control device 4 may be set up in such a way that it regulates movement of robotic arms 2, 3 and/or of the drives.

Robotic surgical system 1 is configured for use on a patient "P" positioned (e.g., lying) on a surgical table "ST" to be treated in a minimally invasive manner by means of a surgical instrument, e.g., electromechanical surgical instrument 200 and, more specifically, end effector 300 of electromechanical surgical instrument 200. Robotic surgical system 1 may include more than two robotic arms 2, 3, the additional robotic arms are likewise connected to control device 4 and telemanipulatable by means of operating console 5. A surgical instrument, for example, electromechanical surgical instrument 200 (including end effector 300 thereof), may also be attached to any additional robotic arm(s).

Control device 4 of robotic surgical system 1 may control one or more motors (not shown), each motor configured to drive movement of robotic arms 2, 3 in any number of directions. Control device 4 may control an instrument drive unit 110 including one or more motors 50 (or motor packs). Motors 50 drive various operations of end effector 300 of electromechanical surgical instrument 200. Motors 50 may include a rotation motor, such as, for example, a canister motor. One or more of motors 50 (or a different motor, not shown) may be configured to drive a rotation of electromechanical surgical instrument 200, or components thereof, relative to a longitudinal axis "L-L" thereof. The one or more motors can be configured to effect operation and/or movement of electromechanical end effector 300 of electromechanical surgical instrument 200.

Figure 2:
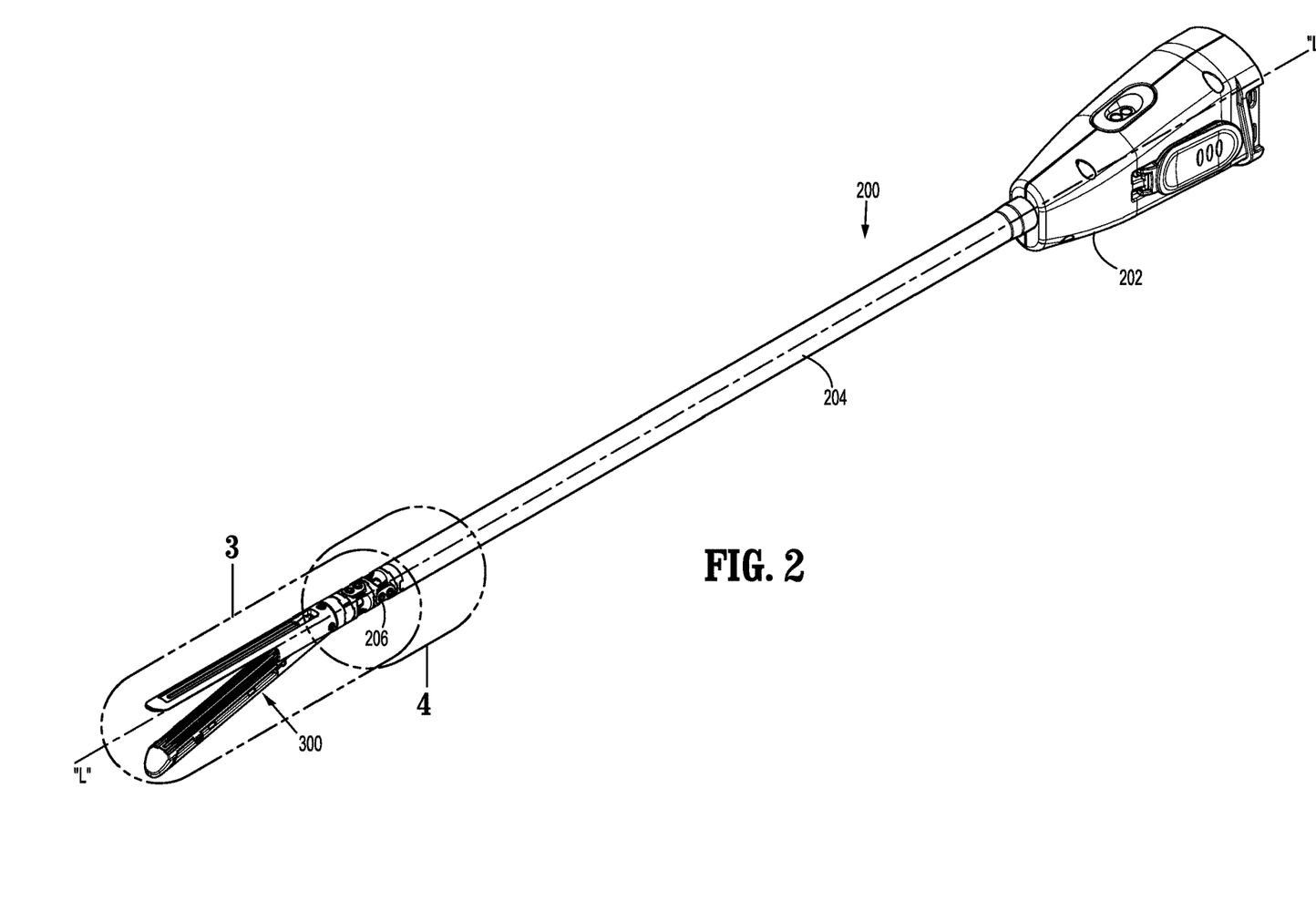
FIG. 2 is a perspective view of a surgical instrument of the robotic surgical system of FIG. 1 in an unarticulated position.

Turning now to FIG. 2, electromechanical surgical instrument 200 of robotic surgical system 1 includes a housing 202 at a proximal end portion thereof and an elongated shaft 204 that extends distally from housing 202. Elongated shaft 204 includes a wrist assembly 206 supported on a distal end portion of elongated shaft 204 that couples end effector 300 to elongated shaft 204.

Housing 202 of electromechanical surgical instrument 200 is configured to selectively couple to instrument drive unit 110 of robotic surgical assembly 100, for example, via side loading on a sterile interface module 112 of robotic surgical assembly 100, to enable motors 50 of instrument drive unit 110 of robotic surgical assembly 100 to operate end effector 300 of electromechanical surgical instrument 200. Housing 202 of electromechanical surgical instrument 200 supports a drive assembly 203 (FIG. 3) that mechanically and/or electrically cooperates with motors 50 of instrument drive unit 110 of robotic surgical assembly 100.

Figure 3:
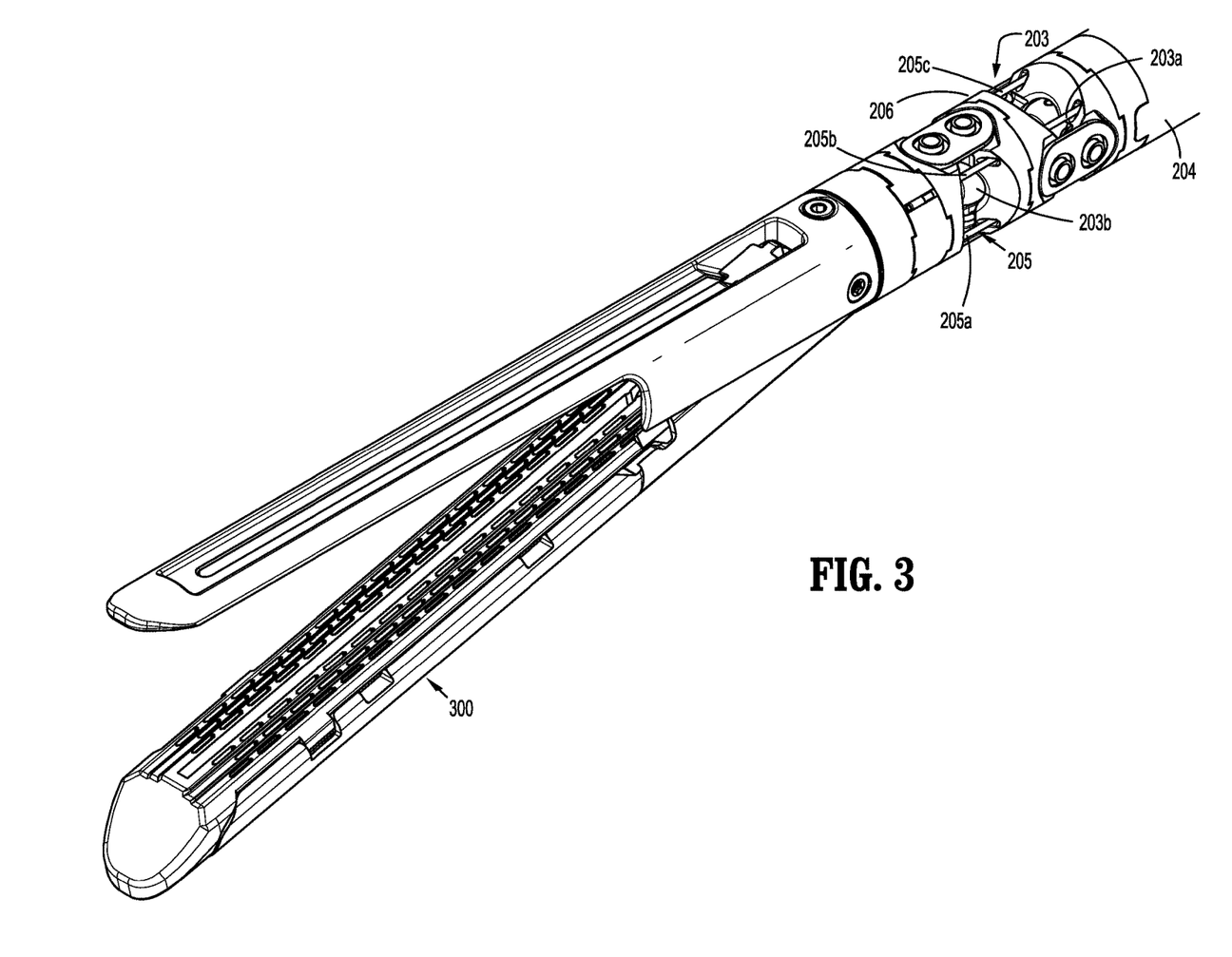
FIG. 3 is an enlarged, perspective view of the indicated area of detail shown in FIG. 2.
Figure 4:
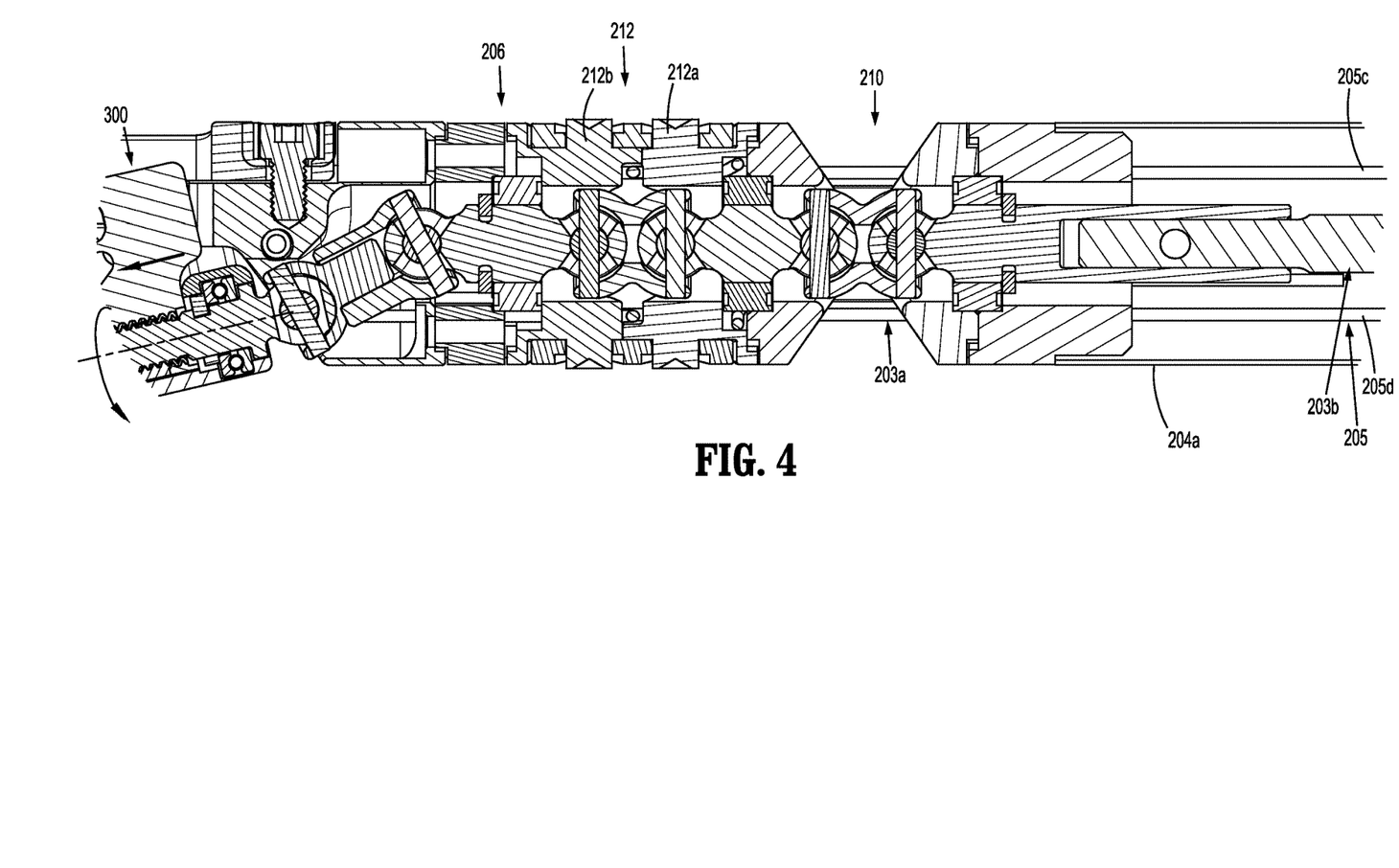
FIG. 4 is an enlarged, longitudinal, cross-sectional view of the indicated area of detail shown in FIG. 2.

Drive assembly 203 of electromechanical surgical instrument 200 can include any suitable electrical and/or mechanical component to effectuate driving force/movement, and which components may be similar to components of the drive assembly described in commonly owned International Application Publication No. WO2017053358, filed Sep. 21, 2016, the entire disclosure of which is incorporated by reference herein. In particular, as seen in FIGS. 3 and 4, drive assembly 203 of electromechanical surgical instrument 200 includes a cable drive assembly 203a and a firing assembly 203b. The cable drive assembly 203a is similar to that described in commonly owned U.S. Patent Application Publication No. 2015/0297199, filed Oct. 22, 2015 and entitled "Adapter Assembly with Gimbal for Interconnecting Electromechanical Surgical Devices and Surgical Loading Units, and Surgical Systems Thereof," the entire disclosure of which is incorporated by reference herein.

As seen in FIGS. 3 and 4, cable drive assembly 203a of electromechanical surgical instrument 200 includes cables 205, such as cables 205a, 205b, 205c, and 205d, which are coupled to a respective driven member (not shown) of electromechanical surgical instrument 200 at a proximal end portion thereof. Cables 205 of cable drive assembly 203a extend distally to distal end portions thereof, and may include ferrules (not shown) that couple to wrist assembly 206 of elongated shaft 204 at circumferentially spaced apart locations (e.g., angularly displaced) about the longitudinal axis "L-L" to enable cables 205 to effectuate an articulation/rotation/pitch/yaw of wrist assembly 206 of electromechanical surgical instrument 200 and end effector 300 of electromechanical surgical instrument 200 upon actuation of one or more of cables 205. Cable drive assembly 203a can include one or more pulleys, friction wheels, gears, couplers, rack and pinion arrangements, etc. coupled directly or indirectly to the driven members and/or cables 205 to facilitate driving movement imparted through the driven members and/or cables 205. The cables 205 can be arranged such that diagonal cables (e.g. cables 205d, 205b or cables 205a, 205c; see FIGS. 3 and 4) can be positioned to be driven in opposite directions in order to provide articulation in multiple axes (e.g. two). Although only four cables are shown, cable drive assembly 203a can include any number of cables, for example, to provide additional functionality at the end effector 300.

For a more detailed description of components of exemplar end effectors similar to end effector 300, reference can be made to U.S. Patent Application Publication Nos. 2016/0242779 and 2015/0297199, the entire disclosures of each of which are incorporated by reference herein.

Figure 5:
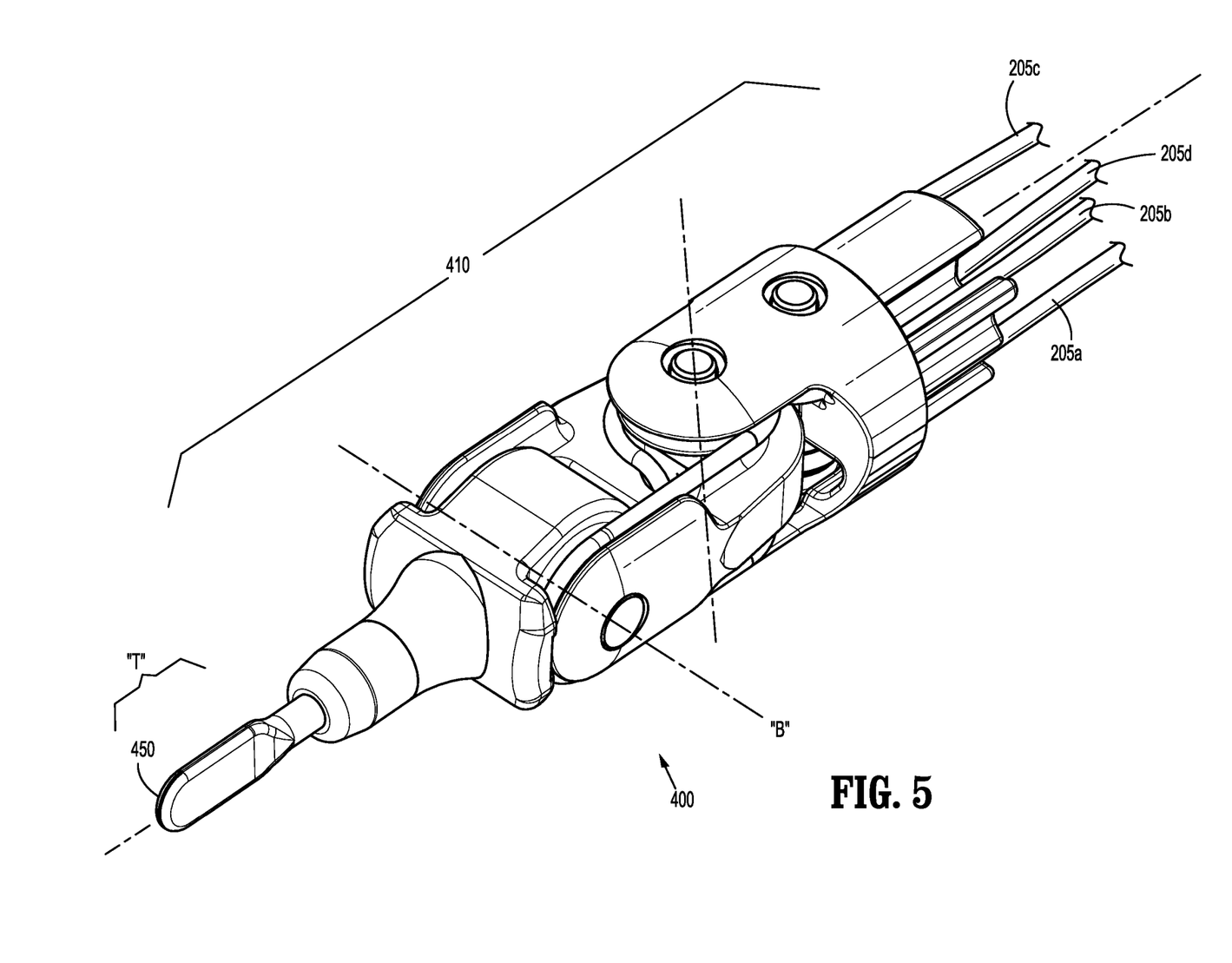
FIG. 5 is a top, perspective view of an end effector including a monopolar tool, according to an embodiment of the present disclosure, for use in the robotic surgical system of FIG. 1.

With reference to FIG. 5, the electromechanical surgical instrument 200 may be configured to support or actuate an end effector 400, in the form of an electrosurgical tool, for example, a monopolar (shown) or bipolar instrument (not shown). End effector 400 is composed of a wrist assembly 410 and a medical instrument, surgical tool or blade "T." The wrist assembly 410 is configured to articulate such that the surgical tool "T" may be positioned or moved by control device 4 (FIG. 1). Surgical tool "T" may be a monopolar electrosurgical device (for example, a blade 450) electrically coupled to an electrosurgical generator "G" (FIG. 1) via a power cable. Electrosurgical generator "G" is configured to generate electrosurgical radio frequency energy and transmit the generated electrosurgical radio frequency energy to surgical tool 450 of end effector 400 for treatment of tissue via the power cable. For a more detailed description of components of exemplar end effectors similar to end effector 400, reference can be made to U.S. patent application Ser. No. 16/636,247, filed on Feb. 3, 2020, the entire disclosure of which is incorporated by reference herein.

In accordance with the present disclosure, electromechanical surgical instrument 200 may be configured for insertion through a natural body orifice of the human body (e.g., relatively larger lumen), such as, for example, trans-esophageal or trans-anal, depending on the needs of the surgical procedure. When operating within or through a natural body orifice, it is desirable for the electromechanical surgical instrument to be configured for omni-directional flexing and/or steering in order to navigate through the tortuous pathways of the orifice.

Figures 6, 7:
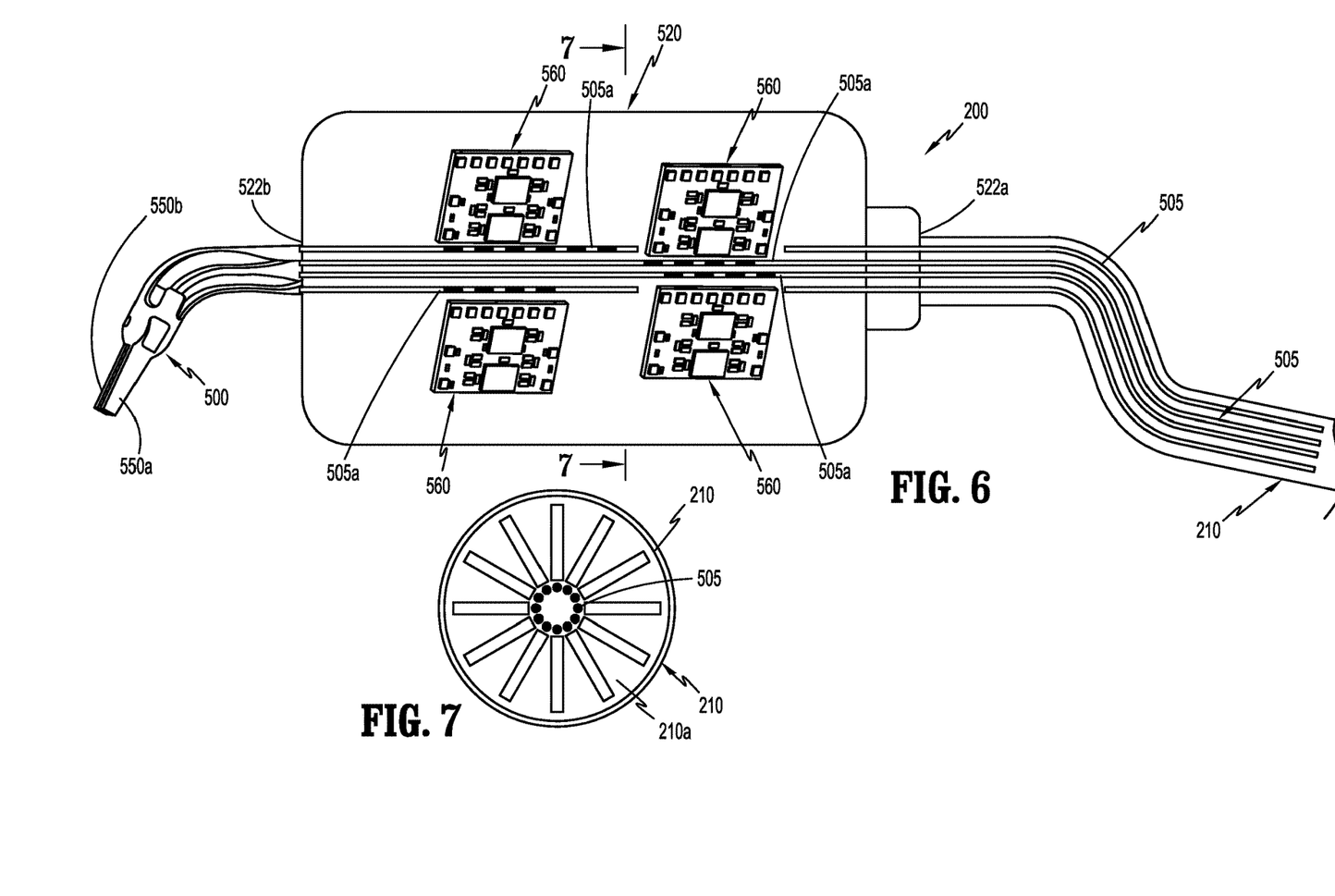
FIG. 6 is a schematic, cross-sectional illustration of a distal end portion of a surgical instrument in accordance with this disclosure.
FIG. 7 is a transverse, cross-sectional view of the distal end portion of the surgical instrument illustrated in FIG. 6, as taken through 7-7 of FIG. 6.

With reference to FIGS. 6 and 7, the electromechanical surgical instrument 200 of the present disclosure is particularly suited for use in natural body orifices (e.g., relatively larger lumens) of the human body. Electromechanical surgical instrument 200 may include an elongate flexible shaft 210 defining a lumen 210a therethrough. Electromechanical surgical instrument 200 is configured to support an end effector or tool 500 at a distal end of the elongate flexible shaft 210. End effector 500 may take the form of a grasper, forceps or the like, including a pair of jaws 550a, 550b. Electromechanical surgical instrument 200 includes a plurality of cables, push/pull rods or a combination thereof 505 slidably extending through the lumen 210a of the flexible shaft 210. As mentioned above, a proximal end of the plurality of cables or push/pull rods 505 may be operatively connected to a respective driven member (not shown) of electromechanical surgical instrument 200, and a distal end of the plurality of cables or push/pull rods 505 may be operatively connected to ferrules (not shown) that couple to a wrist assembly of the electromechanical surgical instrument 500 to effectuate an articulation/rotation/pitch/yaw of the wrist assembly of electromechanical surgical instrument 200 and/or end effector 500 of electromechanical surgical instrument 200 and/or of the pair of jaws 550a, 550b. For a more detailed description of components of exemplar end effectors similar to end effector 500, reference can be made to U.S. Pat. Nos. 10,258,359, 10,390,853, the entire disclosure of each of which being incorporated by reference herein.

It is contemplated that the plurality of cables or push/pull rods 505 may be fabricated from tungsten and/or nitinol (e.g., a nickel-titanium alloy), or the like. While four (4) to twelve (12) cables or push/pull rods 505 are shown, it is contemplated that any number of cables or push/pull rods 505 may be used without departing from the present disclosure. In practice, coordinated, reciprocal translation of four (4) cables or push/pull rods 505 is used to achieve full range of pitch/yaw pivoting for an end effector of one electromechanical surgical instrument; while coordinated, reciprocal translation of eight (8) cables or push/pull rods 505 is used to achieve full range of pitch/yaw pivoting for end effectors of two electromechanical surgical instruments; and coordinated, reciprocal translation of twelve (12) cables or push/pull rods 505 is used to achieve full range of pitch/yaw pivoting for end effectors of three electromechanical surgical instruments; where the electromechanical surgical instruments and/or end effectors may include forceps, graspers, staplers, spatulas, blades, dissectors, energy-based devices (e.g., such as the LIGASURE® Vessel Sealing Generator and forceps/instruments, and the Force Triad® Generator as sold by Covidien), scopes, cameras, and the like.

With continued reference to FIGS. 6 and 7, electromechanical surgical instrument 200 includes a capsule, collar or hub 520 supported on flexible shaft 210, at a location in relative close proximity to end effector 500. Capsule 520 may be rigid, wherein the flexible shaft 210 extends from a proximal and distal end of the capsule 520, or flexible, wherein the flexible shaft 210 may form a part of the capsule 520. It is contemplated that the capsule 520 and the flexible shaft 210 may be sealed (e.g., hermetically sealed) at the interfaces 522a, 522b therebetween, at both the proximal end and the distal end of the capsule 520.

Within capsule 520, each cable or push/pull rod 505 is provided with discrete, uniform length, metrical markings 505a along a length of respective cables or push/pull rods 505. Metrical markings 505a may be uniform in length (e.g., a uniform linear array) or may have varying lengths and/or distributions along a length of respective cables or push/pull rods 505. For example, a frequency of metrical markings 505a may increase while an individual length of metrical markings 505a decrease near a proximal or distal region thereof. As can be appreciated, in accordance with the present disclosure, and in addition to the details to be discussed below, this change in frequency and individual length of metrical markings 505a may communicate certain information to control device 4 of robotic surgical system 1, such as, for example, if the pair of jaws 550a, 550b are approaching a maximum end of pitch/yaw thereof.

In accordance with the present disclosure, electromechanical surgical instrument 200 includes a plurality of linear encoders 560 (e.g., one linear encoder for each cable or push/pull rod 505) supported within capsule 520 and being in registration with respective metrical markings 505a. While four (4) to twelve (12) linear encoders 560 are shown, it is contemplated that any number of linear encoders 560 may be used without departing from the present disclosure.

The linear encoders 560 are configured to observe/monitor the metrical markings 505a of respective cable or push/ pull rod 505 and communicate or transmit information (e.g., individual lengths of the metrical marks 505*a* and/or distances between adjacent metrical marks 505*a*) to control device 4 of robotic surgical system 1. This information is processed by control device 4, and control device 4 may make adjustments to control signals delivered to motors 50 of instrument drive unit 110 of robotic surgical assembly 100, which in turn control axial translation of cables or push/pull rods 505.

In use, as cable or push/pull rod 505 are actuated or translated, a location of the metrical marks 505*a* and/or a relative displacement of the cables or push/pull rods 505 may be observed, measured and/or recorded by the linear encoders 560. Alternatively or additionally, over time, as cable or push/pull rod 505 are actuated, tensile forces acting on cable or push/pull rod 505 may cause the overall lengths of cable or push/pull rod 505 to increase, which would be reflected in the specific lengths of the metrical marks 505*a* and/or distances between adjacent metrical marks 505*a* and/or displacement of the cables or push/pull rods 505. These changes in lengths of the metrical marks 505*a* and/or distances between adjacent metrical marks 505*a*, as observed by linear encoders 560, are communicated/transmitted to control device 4 of robotic surgical system 1, and control device 4 may once again, and continuously send adjusted control signals to motors 50 of instrument drive unit 110 of robotic surgical assembly 100 to account for these changes, and to ensure that the pitch/yaw and/or actuation of the end effector remains accurate (or within acceptable tolerances).

Figure 8:
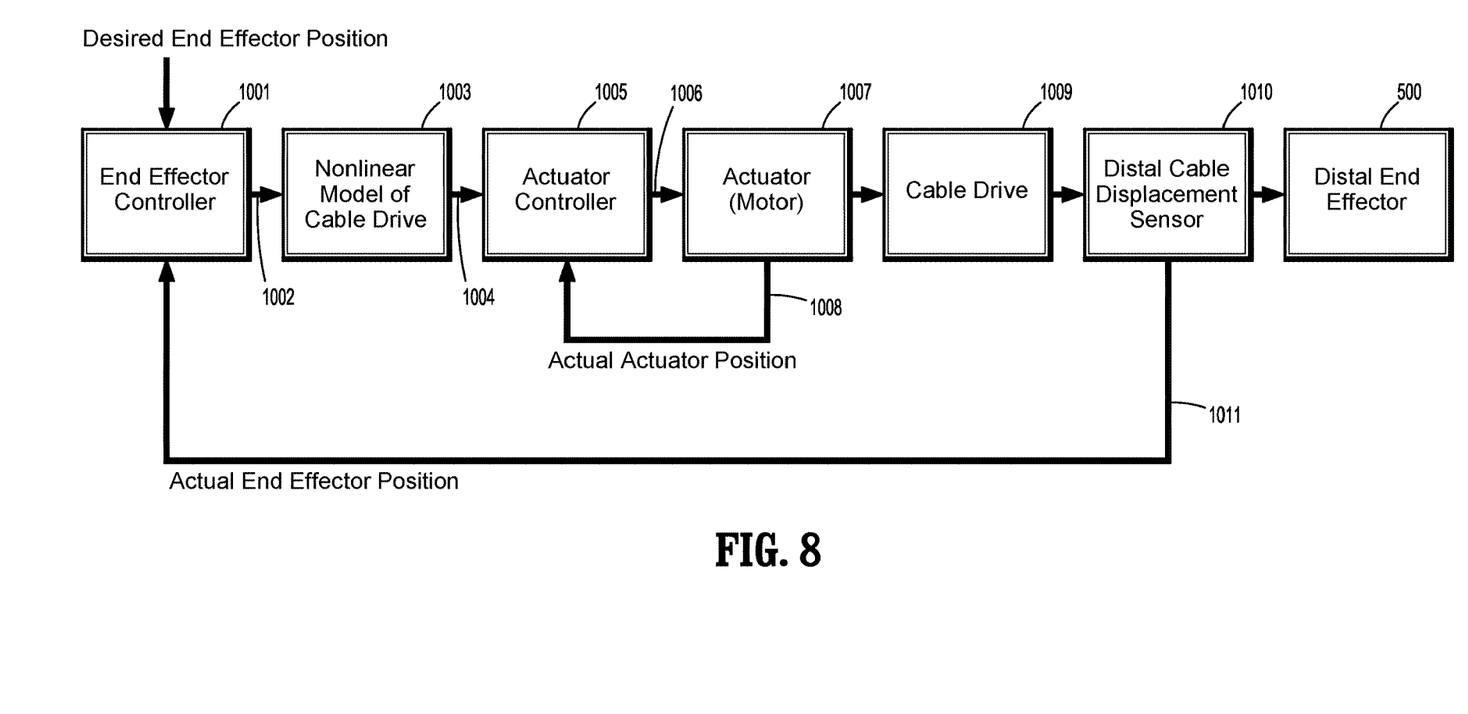
FIG. 8 is a block diagram of a nonlinear control and sensing scheme in accordance with the present disclosure.

With reference to FIG. 8, a nonlinear control and sensing scheme, in accordance with the present disclosure, is illustrated. In accordance with the present disclosure, a desired position of an end effector (e.g., end effector 500) is generated by a high level motion controller (e.g. teleoperated master-slave system or automated motion profile or control device 4). A signal containing this desired end effector position is sent to an end effector position controller 1001 and is compared with an actual end effector position 1011 that is measured by a distal cable displacement sensor 1010. The controller or control device 4 computes a position error and combines, at 1002, the position error with additional control signals that are inputs to a nonlinear model 1003 of a cable drive (e.g., cable or push/pull rod 505). This nonlinear model 1003 of the cable drive determines a desired displacement of a proximal end of a cable drive required to overcome nonlinearities such as backlash, cable stretch, stiction, and changes in length of the cable path due to bending, to effect a desired distal end movement of end effector 500. This desired proximal position of the proximal end of the cable drive is then used or communicated, at 1004, as an input to the actuator controller 1005 which computes commanded current commands, at 1006, for actuator 1007 (e.g., motor(s) 50 of instrument drive unit 110 of robotic surgical assembly 100).

The actuator controller 1005 is typically a position controller using a feedback loop 1008 from the actual position of the actuator 1007 measured by an encoder (e.g., linear encoder 560) in the actuator 1007. The actuator 1007 is connected to a mechanism that pulls on the cables (e.g., cable or push/pull rod 505) in a cable drive 1009 that transmits the motion through the flexible conduit or shaft 210 to the distal end of the device or the electromechanical surgical instrument 200. The distal cable displacement sensor 1010 measures the actual position of the cable (e.g., cable or push/pull rod 505) and is used as an approximation of the actual position 1011 (pitch/yaw) of the end effector 500.

The nonlinear model 1003 of the cable drive greatly improves the performance of the robotic surgical system and/or the electromechanical surgical instrument because the nonlinear model 1003 compensates for any nonlinearities and allows a linear feedback controller (e.g., linear encoder 560) to be used. Closing the feedback loop without this would result in a relatively slower response, inaccuracies, and relatively greater variation in performance as the flexible conduit or shaft 210 changes shape and/or is flexed/bent/steered.

In accordance with the present disclosure, it is further contemplated that vision based algorithms may be used with video captured by an endoscope to close an additional feedback loop to provide additional control accuracy for movements of the end effector 500.

Additionally, the linear encoders 560 and the nonlinear control and sensing scheme described above may be used in addition to or in place of a distal cable displacement sensor.

Further, an adaptive nonlinear control and sensing scheme for the cable drive, that automatically adjust control parameters to compensate for observable parameters (that slowly change over time), may be used to monitor overall curvature changes to the flexible shaft 210.

It is contemplated that a neural network or other artificial intelligence based algorithm may be used to develop and implement the nonlinear control and sensing scheme for the cable drive. The nonlinear control and sensing scheme for the cable drive may be taught based on a robust data-set of commanded motions and observed (e.g., measured) end effector positions.

It is still further contemplated that measured tension on the cable or push/pull rod 505 may be used as an additional input to the controller or control device 4 to provide increased control for the end effector and an increased ability to estimate applied forces and torque acting on tissue by the end effector 500. For example, tension on the cable or push/pull rod 505 may be estimated by comparing a translation of the cable or push/pull rod 505 at a distal end thereof with a translation of the cable or push/pull rod 505 at a proximal end thereof.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An electromechanical robotic surgical instrument, comprising:
 a flexible shaft defining a lumen therethrough;
 an end effector pivotally supported by the flexible shaft;

at least one cable translatably disposed within the lumen of the flexible shaft, wherein a distal end of each cable is operatively connected to the end effector to affect a movement of the end effector in response to translation of the at least one cable, wherein the at least one cable includes metrical markings along an outer surface thereof, which metrical markings are located adjacent to the end effector, wherein each metrical marking has a length; and at least one linear encoder supported by the flexible shaft and being in operative registration with the metrical markings of a respective one of the at least one cable, wherein the at least one linear encoder is configured to measure changes in the length of each metrical marking as a respective underlying cable stretches during use.

2. The electromechanical robotic surgical instrument according to claim 1, further comprising a capsule interconnecting the end effector and a distal end of the flexible shaft, wherein the metrical markings of the at least one cable are disposed within the capsule.

3. The electromechanical robotic surgical instrument according to claim 2, wherein the at least one linear encoder is disposed within the capsule.

4. The electromechanical robotic surgical instrument according to claim 2, wherein the end effector is in sealed engagement with the capsule.

5. The electromechanical robotic surgical instrument according to claim 2, wherein the distal end of the flexible shaft is in sealed engagement with the capsule.

6. The electromechanical robotic surgical instrument according to claim 2, wherein the at least one linear encoder is configured to command a change in a translation of the at least one cable based on changes exhibited by the metrical markings.

7. The electromechanical robotic surgical instrument according to claim 1, further comprising a motion controller configured to carry out a nonlinear control and sensing scheme comprising:
   generating a desired position of the end effector;
   sending a signal, containing the desired position of the end effector, to an end effector position controller;
   comparing the desired position of the end effector to an actual position of the end effector as measured by a displacement sensor;
   computing a position error between the desired position and the actual position of the end effector;
   combining the position error with additional control signals inputs for a nonlinear model for the at least one cable, wherein the nonlinear model determines a desired displacement of a proximal end of the at least one cable to overcome at least one of nonlinearities or changes in a length of the at least one cable; and
   inputting the desired displacement of the proximal end of the at least one cable to an actuator for translating the at least one cable.

8. An electromechanical robotic surgical instrument, comprising:
   a shaft defining a lumen therethrough, wherein the shaft is flexible along at least a proximal portion thereof;
   an end effector pivotally supported at a distal end of the shaft;
   at least one cable translatably disposed within the lumen of the shaft, wherein a distal end of each cable is operatively connected to the end effector to affect a movement of the end effector in response to translation of the at least one cable, wherein the at least one cable includes metrical markings along an outer surface thereof, which metrical markings are located adjacent to the end effector and distal of the flexible proximal portion of the shaft, wherein each metrical marking has a length; and
   at least one linear encoder supported by the shaft at a location between the flexible proximal portion of the shaft and the distal end of the shaft, each linear encoder being in operative registration with the metrical markings of a respective one of the at least one cable, wherein each linear encoder is configured to measure changes in the length of each metrical marking as a respective underlying cable stretches during use.

9. The electromechanical robotic surgical instrument according to claim 8, further comprising a capsule interconnecting the end effector and the distal end of the shaft, wherein the metrical markings of the at least one cable are disposed within the capsule.

10. The electromechanical robotic surgical instrument according to claim 9, wherein the at least one linear encoder is disposed within the capsule.

11. The electromechanical robotic surgical instrument according to claim 9, wherein the end effector is in sealed engagement with the capsule.

12. The electromechanical robotic surgical instrument according to claim 9, wherein the distal end of the shaft is in sealed engagement with the capsule.

13. The electromechanical robotic surgical instrument according to claim 9, wherein the at least one linear encoder is configured to command a change in a translation of the at least one cable based on changes exhibited by the metrical markings.

* * * * *